US012616815B1

(12) United States Patent
Prashad et al.

(10) Patent No.: US 12,616,815 B1
(45) Date of Patent: May 5, 2026

(54) INTRAVENOUS CATHETER REINFORCED TO MAINTAIN VOLUMETRIC INTEGRITY

(71) Applicants: Akash R. Prashad, Ocala, FL (US); Garen Manoogian, Ocala, FL (US)

(72) Inventors: Akash R. Prashad, Ocala, FL (US); Garen Manoogian, Ocala, FL (US)

(73) Assignee: American Medical Advancement, LLC, Ocala, FL (US)

( * ) Notice: Subject to any disclaimer, the term of this patent is extended or adjusted under 35 U.S.C. 154(b) by 94 days.

(21) Appl. No.: 16/740,367

(22) Filed: Jan. 10, 2020

(51) Int. Cl.
*A61M 25/00* (2006.01)
*A61L 29/04* (2006.01)

(52) U.S. Cl.
CPC ......... *A61M 25/005* (2013.01); *A61L 29/049* (2013.01); *A61M 25/0097* (2013.01)

(58) Field of Classification Search
CPC ............ A61M 25/005; A61M 25/0097; A61M 25/0662; A61M 25/0021; A61L 29/049
See application file for complete search history.

(56) References Cited

U.S. PATENT DOCUMENTS

| | | | | |
|---|---|---|---|---|
| 2,467,559 A | * | 4/1949 | Mahlberg | F16L 11/02 |
| | | | | 138/131 |
| 4,368,730 A | * | 1/1983 | Sharrock | A61M 25/00 |
| | | | | 604/524 |
| 4,572,186 A | * | 2/1986 | Gould | A61M 29/02 |
| | | | | 604/103.09 |
| 5,057,092 A | * | 10/1991 | Webster, Jr. | A61M 25/005 |
| | | | | 138/123 |
| 5,190,520 A | * | 3/1993 | Fenton, Jr. | A61M 25/005 |
| | | | | 604/43 |
| 5,484,425 A | * | 1/1996 | Fischell | A61M 25/005 |
| | | | | 600/435 |
| 6,217,566 B1 | * | 4/2001 | Ju | A61M 25/005 |
| | | | | 604/526 |
| 6,228,073 B1 | * | 5/2001 | Noone | A61M 25/0014 |
| | | | | 128/912 |
| 6,355,027 B1 | * | 3/2002 | Le | A61M 25/0054 |
| | | | | 604/525 |
| 2016/0101262 A1 | * | 4/2016 | Root | A61M 25/005 |
| | | | | 604/510 |

* cited by examiner

*Primary Examiner* — Michael J Tsai
*Assistant Examiner* — Neeraja Gollamudi
(74) *Attorney, Agent, or Firm* — Weisberg I.P. Law, P.A.

(57) ABSTRACT

An intravenous (IV) catheter having a cannula with a length of tubing with sidewalls reinforced by a radial force element. The radial force element is formed by a material different from a uniform material that forms the exposed external surface of the tubing and the interior surface of the tubing through which fluids flow. The radial force element distributes a perpendicular external force applied to a point of the length of tubing across a surface area of the tubing, which minimizes decreases in the interior diameter of the tubing at the point compared to a substantially equivalent tubing lacking the radial force element.

21 Claims, 4 Drawing Sheets

Introducer Needle  105

Needle Hub  110

Catheter  115

Catheter Hub  120

Intravascular (IV) Catheter

125

Insertion Point

155

120

Dressing  150

115

Skin
135

Subcutaneous
Tissue
140

Vessel
145

200

External Force
210

Kink Area
(Terminal Section)

Proximal Direction

Kink 215

Inner Diameter 220

Distal Direction

IV Catheter 205

225

External Force
240

Reinforcing Member
235

Dynamically-Reinforced IV Catheter
230

<u>Longitudinal Cross-Section   300</u>
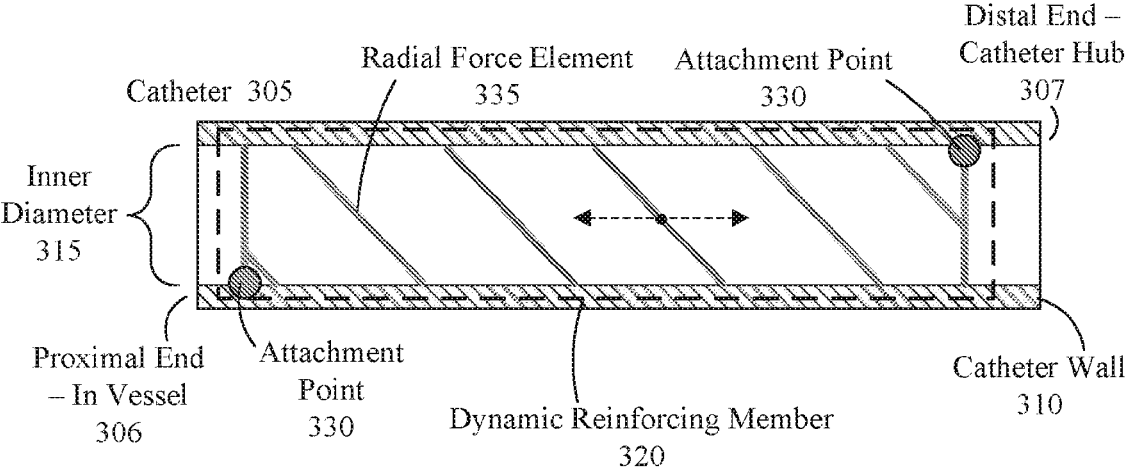
Distal End –
Catheter Hub
307
Radial Force Element        Attachment Point
335                         330
Catheter  305
Inner
Diameter
315
Proximal End
– In Vessel
306
Attachment
Point
330
Dynamic Reinforcing Member
320
Catheter Wall
310
FIG. 3A
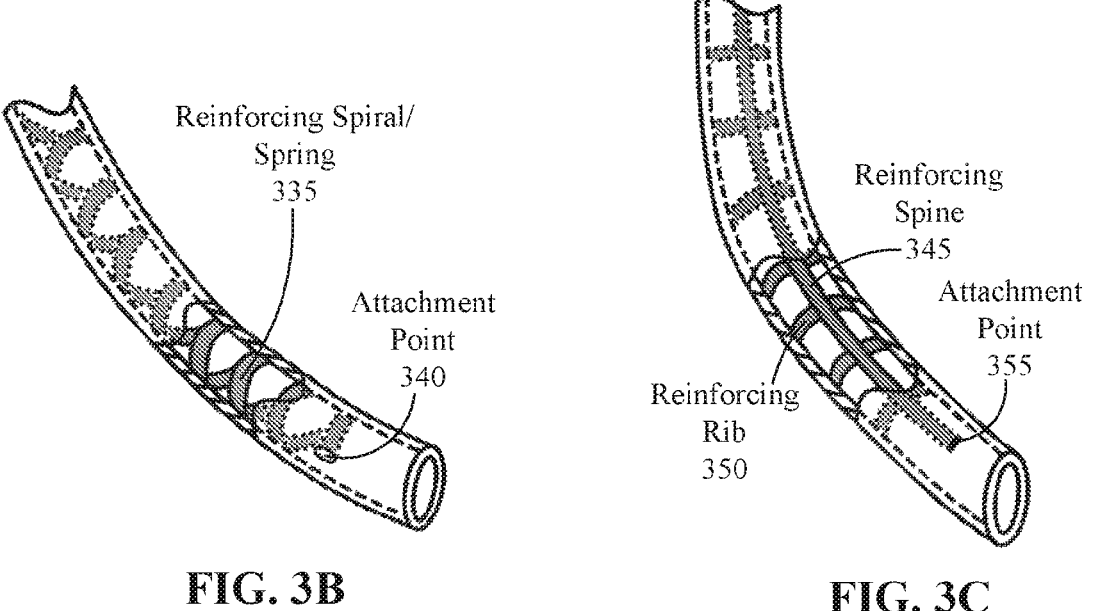
Reinforcing Spiral/
Spring
335
Attachment
Point
340
Reinforcing
Spine
345
Attachment
Point
355
Reinforcing
Rib
350
FIG. 3B                    FIG. 3C

| Characteristics | Silicone | PolyUrethane | PolyEthylene | Teflon/PTFE |
|---|---|---|---|---|
| CATHETER MATERIALS COMPARISON | | | | |
| ID Ratio | Thicker Wall/ID Smaller | Thinner Wall/ID Larger | Thicker Wall | Thicker Wall |
| Biocompatibility | Excellent | Excellent | Fair | Fair |
| Compatibility | Non-Reactive | Non-Reactive | Non-Reactive | Non-Reactive |
| Heat Sensitivity | Excellent | Poor | Excellent | Excellent |
| Stiffness | Soft | Softens in body | Stiff | Stiff |
| Ease of Insertion | More Difficult | Moderately Easy | Easy | Easy |
| Ease of Modifying | Easy | Fair | Poor | Difficult |
| Memory | Excellent | Poor | Poor | Poor |
| Tensile Strength | Fair | Excellent | Excellent | Excellent |
| Flexibility | Excellent | Moderate | Poor-Rigid | Poor-Rigid |
| Coefficient of Friction | Fair | Excellent | Good | Excellent |
| Coating Option | More Difficult | Hydromer | n/a | n/a |
| Sterilization Method | Autoclave or EtO | EtO | Autoclave or EtO | Autoclave or EtO |

FIG. 4

INTRAVENOUS CATHETER REINFORCED TO MAINTAIN VOLUMETRIC INTEGRITY

BACKGROUND

The present invention relates to the field of medical supplies, and more particularly to an intravascular (IV) catheter reinforced to maintain volumetric integrity.

An intravascular (IV) catheter 125 is a crucial medical device for patient care. FIG. 1A illustrates the two primary components of a typical IV catheter 125, prior to insertion into a patient. The first component is a needle assembly comprised of an introducer needle 105 coupled to a needle hub 110. The second component is a catheter assembly comprised of the catheter 115 coupled to a catheter hub 120. The catheter 115 and catheter hub 120 are of a gauge to fit snuggly over the needle 105 and needle hub 110 to produce the assembled IV catheter 125.

The introducer needle 105 extends past the length of the catheter 115 in order to pierce a patient's skin 135, subcutaneous tissue 140, and vessel 145 wall at a determined insertion point 155, creating a pathway for the catheter 115, as shown in FIG. 1A. The needle 105 is retracted, leaving the catheter 115 embedded in the vessel 145. Depending on the apparatus attached to the hub 110, fluids are then pushed directly into the vessel 145 or blood is drawn directly from the vessel 145.

Despite its high usage, over one-third of the IV catheters 125 administered (in the United States) will fail in some manner before the end of its required dwell time (normal dwell time 72-96 hours), resulting in its removal and the insertion of a new IV catheter 125. Typical failures include phlebitis, infiltration, occlusion/mechanical failure, dislodgment, infection, and/or various combinations thereof. Therefore, the longer a patient needs an IV catheter 125, the more likely a failure will occur. Medical costs and complications resulting from the need to reinsert IV catheters greatly exceed the costs of the IV catheters themselves and given the relatively large anticipated failure rates of conventional IV catheters 125 minimization of failure rates through catheter improvements represents a significant cost savings overall and significant health improvement returns for patients.

Historically, catheter designers were limited to single material options along the length of the catheter. Reinforced catheters in production occasionally lack the required flexibility at the distal end, while unreinforced catheters sometimes lack the necessary uniformity of rigidity from the proximal end. Nonetheless over the years, a few improvements to the design of the IV catheter 125 have been implemented to reduce failure rates. For example, stabilization apparatuses have been externally attached to address failures due to dislodgement (i.e., prevent the catheter 115 from being removed when pulled upon) or patient movements (i.e., bending or kinking the catheter 115). However, these stabilization apparatuses are not widely used due to their cumbersome nature. Most other attempted improvements have also been external attachments, such as an adhesive dressing 150 to stick the catheter 115 to the proximate skin 135, and not to the catheter 115 itself, save for advances in medical grade materials upon which the tubing is uniformly constructed.

What is needed is a solution that allows the catheter 115 to retain its volumetric integrity in light of external forces, as well as improved cutability, torque transmission, and deformation upon insertion and during patient dwell time.

Such a solution would dynamically reinforce the interior of the catheter 115 in response to external mechanical and fluidic forces.

It should be understood that FIG. 1B as with other drawings presented herein are for illustrative purposes to demonstrate the concepts expressed herein. As such, one of ordinary skill can understand that some simplifications for expression are denoted. For example, in practice, dressings (150) are applied over the cannula, hub, and line even though they are shown as a horizontal plain in FIG. 1B to ensure visibility of significant drawing elements.

BRIEF DESCRIPTION OF THE SEVERAL VIEWS OF THE DRAWINGS

FIG. 3A is a block diagram that presents an enlarged longitudinal cross-section of the dynamically-reinforced IV catheter in accordance with embodiments of the inventive arrangements disclosed herein.

FIG. 3B depicts an example embodiment of the dynamically-reinforced IV catheter having a spiral or spring as the reinforcing member in accordance with embodiments of the inventive arrangements disclosed herein.

FIG. 3C depicts an example embodiment of the dynamically-reinforced IV catheter having a spine with radial ribs as the reinforcing member in accordance with embodiments of the inventive arrangements disclosed herein.

FIG. 4 depicts a general comparison of medical grade catheter materials in accordance with embodiments of the inventive arrangements disclosed herein.

DETAILED DESCRIPTION

Figure 1A:
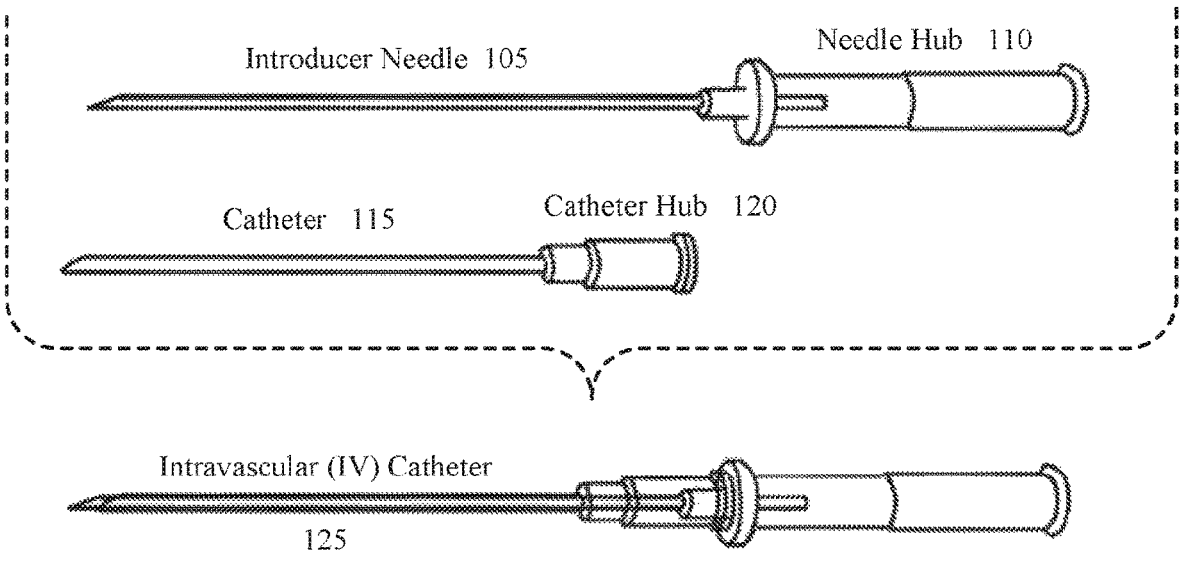
FIG. 1A (PRIOR ART) depicts the basic components of a safety intravenous (IV) catheter.
Figure 1B:
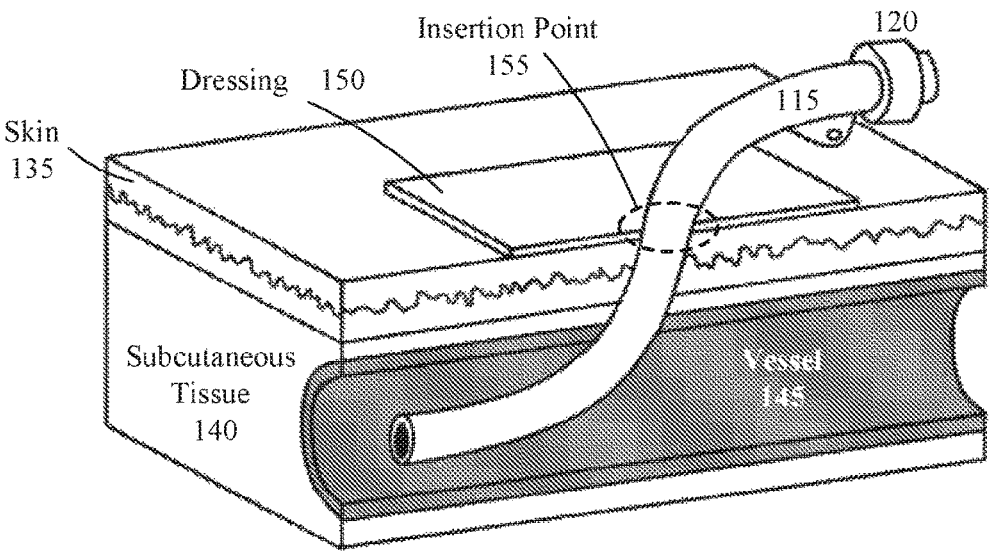
FIG. 1B (PRIOR ART) illustrates the general placement of a safety IV catheter in use.

Embodiments of the disclosed invention can present an intravenous catheter that maintains its volumetric and hemodynamic integrity. That is, without substantially altering the interior or exterior diameters, sidewalls of catheter tubing (cannula) include a radial reinforcing member (generating a radial force along the tubing that is presently lacking) that prevents kinking of the tubing, which may result in typical failures including phlebitis, infiltration, occlusion/mechanical failure, dislodgment, infection, and/or various combinations thereof. Fundamentally, intravenous catheters are positioned on a human body and remain inserted for a substantial period of time. Inevitable movement by the patients concurrently moves the tubing resulting in dynamic forces being exerted upon the tubing, which inherently experiences external pressures by being inserted through the skin and subcutaneous tissue into a vein. Conventional tubing is constrained in size (having a fixed interior and exterior diameter) by its function and external stabilization measures to minimize movement of the tubing can be highly uncomfortable to patients. A balance between flexibility and strength is required for the tubing, as increasing rigidity (and compression resistance at a perpendicular force that distorts the interior of the tubing) typically decreases needed flexibility and usability. Embodiments of the disclosure reinforces the tubing utilizing a reinforcing spiral spring or other radial support element. This spring can be embedded in the sidewall of the tubing to ensure the interior and exterior diameters are unchanged from conventional tubing. That is, a helical pattern forming decompression reinforcements is able to be utilized, which can be sinusoidal, spring, helical, or like shapes—where helical shapes are preferred in some embodiments. Changing the exterior or interior diameter of the tubing results in problems with insertion and use.

For example, changing a diameter of the tubing alters fluid flow. Any inconsistencies in the interior diameter of the tubing provides an obstacle to fluid flow. Given bloods ability to coagulate when not flowing, the blood effectively functions as a solidifying fluid (glue like) so interior diameter changes in the tubing allowing particles or blood to be trapped or fixed results in dangers of clotting, formation of air bubbles, and other harmful side-effects. In embodiments, use of coatings having anticoagulant effects are beneficial as is the use of a hydrophilic lubricious coating. By reinforcing the sidewall using a spiral element, the flexibility of the tubing is maintained while diminishing risks of interior diameter changes due to dynamic movements of patients. To elaborate, the spiral elements permits a level of separation when the catheter is flexed and as it travels through a bodily lumen, such as a vessel. The catheter is thus capable of transmitting an axial, push force against variations of vascular occlusions, complications, and or hemodynamic irregularities.

In embodiments, the tubing sidewalls are made of a semi-compressive material, which coupled with the reinforcing spiral permits a conventionally impossible amount of compression/expansion along the longitudinal length of the tubing that is more forgiving of movement, yet which still protects the interior diameter of the tubing through which fluids flow. While the disclosure contemplates the innovation for any tubing used by an intravenous catheter, in one embodiment, the innovation can be applied to any cannula that is inserted into the body for delivery or removal of a fluid. Reinforcing radial force elements need not span the entire length of the tubing or cannula in all embodiments. Hence, selective re-enforcement at critical sections subject to dynamic pressures affecting an interior diameter is contemplated. In embodiments the radially reinforced tubing for an intravenous catheter (or other cannula) is a direct replacement for a standard catheter having a tip for insertion, wings (although most IV's do not have wings) for manual handling and securing the catheter with adhesives, a valve to allow injunction of drugs, and an end commination that allows connection to an intravenous infusion line and a capping in between uses. The needed is partially retracted and serves as a guidewire for inserting the cannula. Thus, no specialized handling or changes in operating procedure are needed to obtain significant benefits through use of the disclosure's innovations.

One embodiment includes a medical device comprising an intravenous (IV) catheter comprising cannula structures consistent with cannula conventions having a cannula formed from cannula materials. The cannula comprises a length of tubing with sidewalls reinforced by a radial force element. The radial force element is formed by a material different from a uniform material that forms the exposed external surface of the tubing and the interior surface of the tubing through which fluids flow. The radial force element distributes a perpendicular external force applied to a point of the length of tubing across a surface area of the tubing, which minimizes decreases in the interior diameter of the tubing at the point compared to a substantially equivalent tubing lacking the radial force element. In an embodiment, the radial force element is present in the terminal section of the tubing but is not present in at least one fourth of the tubing by length. In an embodiment, the medical device further comprises an elastic section, which is a section of the tubing that is not the terminal section, where the elastic section is longitudinally more compressive and expansive than the terminal section. In an embodiment, the elastic section has an exterior diameter greater than the exterior diameter of the terminal section. In an embodiment, the elastic section has an exterior surface that exposes a coil material forming a helical coil, where an exterior surface of the terminal section does not expose the coil material. An embodiment includes a medical catheter including a length of tubing, a hub component, and a dynamic reinforcing member, where the length of tubing made from a medical grade material, which is a cannula material of a predetermined gauge and wall thickness consistent with cannula conventions commensurate with an intended medical purpose. In the embodiment, the hub component is coupled to one end of the length of tubing to facilitate attachment to ancillary elements. In the embodiment, the dynamic reinforcing member is made from a medical-grade material and installed within an interior space of the length of tubing, where the reinforcing member provides sufficient outwards radial force for the length of tubing to maintain at least eighty percent of its volumetric integrity when expected non-catastrophic forces associated with its use in the intended medical purpose are applied, and where the reinforcing member is coupled to an interior wall of the length of tubing proximate to each end at a specified attachment point, and where the reinforcing member is able to dynamically adjust its position within the interior space between attachment points in response to the expected non-catastrophic forces, decreasing a likelihood that the forces cause the interior space to become impassable. Aspects of the present invention are described below with reference to flowchart illustrations and/or block diagrams of methods and apparatus (systems) according to embodiments of the invention.

Figure 2A:
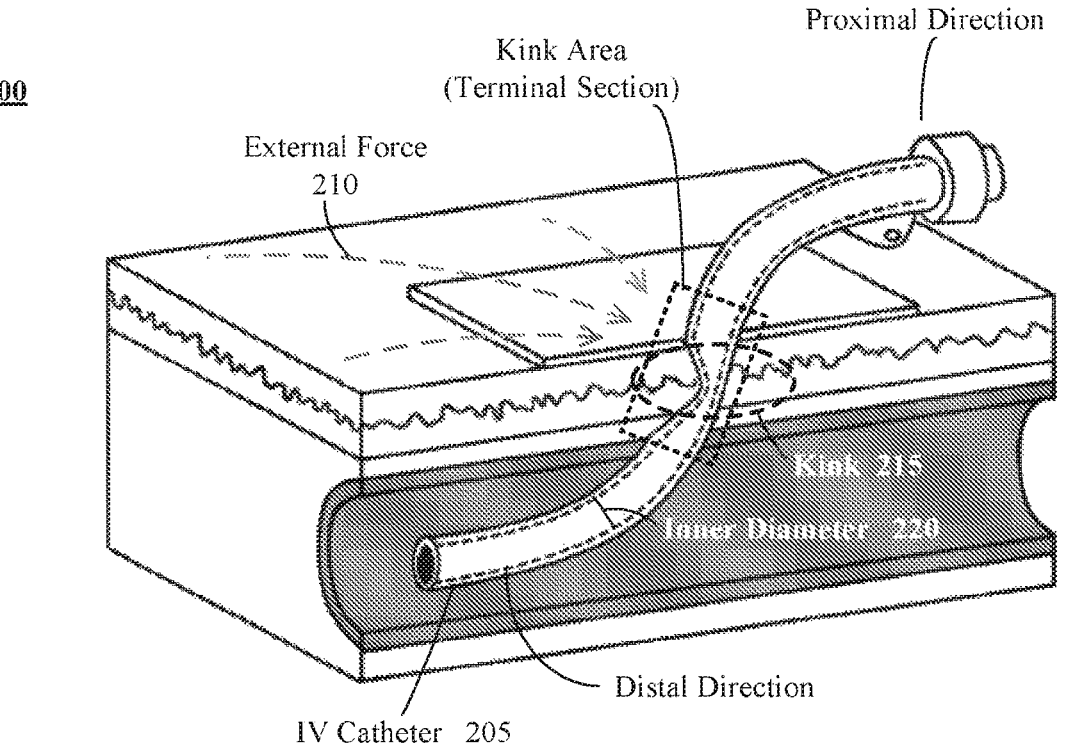
FIGS. 2A and 2B is a collection of illustrations that emphasize the benefit of a dynamically-reinforced IV catheter in accordance with embodiments of the inventive arrangements disclosed herein.
Figure 2B:
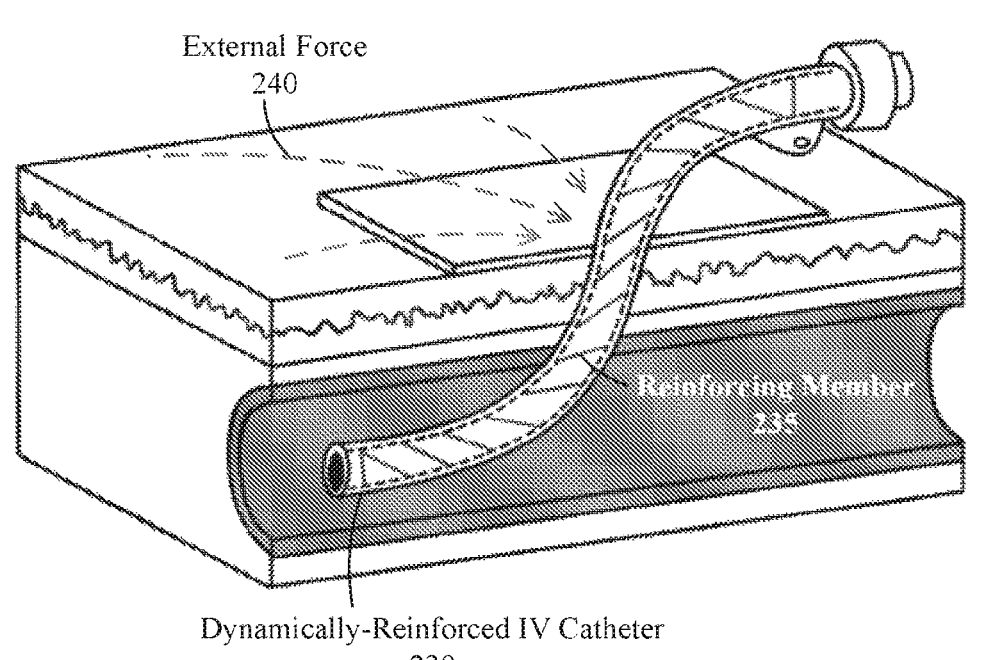

FIGS. 2A and 2B is a collection of illustrations 200 and 225 that emphasize the benefit of a dynamically-reinforced IV catheter 230 in accordance with embodiments of the inventive arrangements disclosed herein. Illustration 200 can present an isometric cross-sectional view of how external forces 210 affect a conventional IV catheter 205. The catheter 205 as shown is a cannula of a peripheral intravascular catheter, although another reinforced cannula is contemplated herein. Further, although shown as being consistently re-enforced throughout its length, embodiments of the cannula are contemplated that have a subsection of their length reinforced where potential problems with kinking are most prevalent.

As shown by the disclosure, an external force 210 affecting the catheter 205 can result from simple patient movements (e.g., bending of arm, hand movement, sleeping, etc.), the motion of other environmental items (i.e., bed sheets, device wires, hospital gown, etc.), physiological changes (i.e., swelling, skin growth, etc.). Kinks 215 occur due to patient movement, other machinery in proximity, poor placement technique (wrong angle of insertion); blood clots can also occur to hematological conditions and are often formed due to kinks 215. A kink 215 is a section of the catheter 205 having a reduced interior diameter 220 that restricts fluid flow relative to the designed inner diameter 220. The labeled kink area of the terminal section represents a segment especially prone to kinks, such as kink 215. Proximal and Distal directions are labeled in FIG. 2A to provide reference directions.

IVs experience positive (put fluids into the body) and negative (take blood out of the body) pressures; negative pressure on a catheter 205 with a kink or narrowing of the inner diameter can cause the catheter to collapse (requires a higher positive pressure to reopen, if it can be reopened, or replacement of the IV). The reinforcing member can dynamically shift with the pressure change to maintain the inner diameter of the catheter.

As shown, the reinforcing member 235 provides a radial force so the catheter maintains its inner diameter against typical external forces—amount of radial force depends on material/design—will still kink if enough external is applied, but should mitigate the amount of force of typical movements. The structural parameters of the catheter are critical in achieving kind-free torqueing and sufficient axial force to cross body lumen blockages, to cross cannula lumen blockages, and/or to minimize harmful flow rate alterations. In practice, the catheter (or cannula) curves at the very points that external force 210 is most prevalent, where a radial reinforcing member 235 helps distribute the perpendicular force applied to the exterior sidewall of the catheter 205 along a portion of the length of the tubing. Thus, the exterior compressive force (external force 240) is not simply being applied to a small subjection (perpendicular region) of the tubing, but is inherently distributed along a wider section, which significantly prevents kinking and related problems. A section of the catheter exposed to external forces resulting from insertion through the skin, subcutaneous tissue and veins, which is a section inserted beyond the insertion point is referred to as the "Insertion Section". A section subject to extreme bends includes not only the Insertion Section, but also the section between the insertion point and the catheter hub 120, which is referred to as the Pre-Insertion Section. The Insertion Section and Pre-Insertion Section together are referable to as the "Terminal Section." Thus, the section provides flexibility and therefore torque response around a bend resulting from decompression, compression, stress, strain, and flow of the fluids at various viscosities with regards to Newtonian and non-Newtonian fluid dynamics. The sections are defined for convenience and simplicity of expression and it should be understood that in practice the tubing may be uniformly or semi-uniformly constructed such that no explicit demarcations exist at the labeled sections (Pre-Insertion, Terminal, and Insertion). In fact, since bends are problematic with regard to exterior forces and since embodiments of the disclosure focus on distributing forces along a larger cross section, the actual division points for the noted sections typically will be constructed to be continuous in structure with adjacent ones of the noted sections.

In one embodiment, the IV catheter 205, 230 other than the radial reinforcement is a direct replacement for a variety of IV cannula created able to be constructed as a standard size (14 to 26 gauge) with a port and wings, with wings without a port, with wings and without a port, with a three way stop cock, without port and with small winds, without a port or wings, with a port, snap fit cap, and suturable wings, without a port and with suturable wings, without a port and with small wings, a gen-type cannula without port and without wings, and the like. Features of the above IV cannula may include flexible wings, biocompatible materials offering longer indwelling times, rounded grips, a non-return silicon value, a transparent flashback chamber, a hydrophobic bacteria retention filter, and the like. As referred to herein, the above types of IV cannula's are collectively referred to as "IV Cannula Structures." Other structures and catheters are considered within scope of the disclosure, which is not limited in this regard in all contemplated embodiments.

In embodiments, the IV catheter 205, 230 conforms to industry pertaining to color coding and size, such that a 14FG catheter is orange, has an interior diameter (I.D) of 1.7 mm, an exterior diameter (O.D.) of 2.1 mm, a catheter length of 45 mm, and a flow rate of 305 ml/min; 16FG catheter is grey, has an I.D. of 1.3 mm, an O.D. of 1.7 mm, a catheter length of 45 mm, and a flow rate of 200 ml/min, 17FG catheter is white, has an I.D. of 1.1 mm, an O.D. of 1.5 mm, a catheter length of 45 mm, and a flow rate of 142 ml/min, 18FG catheter is green, has an I.D. of 0.9 mm, an O.D. of 1.3 mm, a catheter length of 45/32 mm, and a flow rate of 95 ml/min, 20FG catheter is pink, has an I.D. of 0.8 mm, an O.D. of 1.1 mm, a catheter length of 32 mm, and a flow rate of 65 ml/min, 22FG catheter is blue, has an I.D. of 0.6 mm, an O.D. of 0.9 mm, a catheter length of 25 mm, and a flow rate of 36 ml/min, 24FG catheter is yellow, has an I.D. of 0.5 mm, an O.D. of 0.7 mm, a catheter length of 19 mm, and a flow rate of 23 ml/min, 26FG catheter is violet, has an I.D. of 0.45 mm, an O.D. of 0.60 mm, a catheter length of 19 mm, and a flow rate of 17 ml/min. As referred to herein, the above conventions for IV cannula's are collectively referred to as "IV Cannula Conventions." Other structures and catheters are considered within scope of the disclosure, which is not limited in this regard in all contemplated embodiments.

The various medical grade materials used as cannula material are known to have an effect on general vasculitis and cannula usage. Flexibility, durability, chemical compatibility, biocompatibility and thrombogenicity are the characteristics to evaluate when choosing between these materials. In embodiments the cannula material includes silicone, polyurethane (PU), polyethylene (PE), polyvinylchloride (PVC), Polytetrafluoroethylene (PTFE or TEFLON), fluoro ethyl propylene (FEP), and nylon. In general, silicone is more porous than polyurethane and not as durable. Many researchers prefer silicone because it less rigid to the touch and therefore may be less injurious to vessel endothelium. Polyurethane is a thermoplastic and catheters and tubing are extruded. Extruding allows for easy tapering and adjustment of the softness or hardness of the catheter. Catheter tips may be extruded smaller and softer at the tip and larger and more durable outside of the vessel where kinking and abrasion are more likely. Because PU is a thermoplastic, it softens when warmed (by the body or blood) and stiffens when cooled. Catheters therefore will be stiffer outside of the body than they will inside the vessel. Because it is stronger than silicone catheter walls made with PU can be made thinner providing a larger internal diameter than silicone catheter of the same size. This provides better flow and may lessen the chances of clotting-off. All polyurethane is not the same and there are hundreds of polyurethane elastomers available in the market today. IV Cannula of various materials are often sterilized by EO (Ethylene Oxide) gas. A general comparison of medical grade catheter material is provided in FIG. 4. Ideal catheter material has high tensile strength, is soft and pliable, is inherently chemical resistant, is biocompatible, and meets flow requirements while maintaining a minimally invasive circumference, which results in significant requirements of materials and competing strengths/and weaknesses. The radial force element providing increased strength result in a hybrid or combination of the above materials being utilized. Further, reinforcing materials, including metals, which are embedded in the sidewalls between the I.D. and O.D. of the catheter (yet by being sidewall embedded materials are not being exposed to interior fluids or exterior contact) are contemplated as being included. As referred to herein, the above medical grade set of IV cannula materials are collectively referred to as "IV Cannula Material." Other materials are considered within scope of the disclosure, which is not limited in this regard in all contemplated embodiments.

FIG. 3A is a block diagram that presents an enlarged longitudinal cross-section of the dynamically-reinforced IV catheter in accordance with embodiments of the inventive arrangements disclosed herein. In one embodiment, the catheter sections shown in FIGS. 3A, 3B, and 3C are shown for simplicity and are intended to be adapted by the Cannula Structures, consistent with the Cannula Conventions, and are formed from the Cannula Materials, as defined herein.

As shown in longitudinal cross-section 300, the catheter section 305 is a tubing having a uniform inner diameter 315, which ensures consistent fluid flow. The catheter section 305 also has a uniform outer diameter, which ensures an ability to insert the catheter section 305 in a patient. The catheter wall 310 includes the dynamic reinforcing member 320 and/or the radial force element 335. The proximal end 306 is the part of the Insertion Section that is inserted into a vessel. The distal end of the section 300 is the end closest to the catheter hub 307. In one embodiment, the radial force element 335 is connected to the catheter wall 310 at two different attachment points 330. In one embodiment, the radial force element 335 may be attached to the inner tube wall at only its ends via the attachment points 330, which allows the reinforcing members 320 to move "freely" along the inner surface of the wall responsive to pressure changes and movement of the catheter. This increases force distribution of perpendicular external forces (or external radial forces), which prevents compression of an inner diameter of the catheter 305. In a "floating" embodiment having a dynamic reinforcing member 320 as part of the radial force element 335, the interior member 320 must be designed to not impede the fluid flow. Specifically, the materials used for such a member 320 may be expressly designed or coated to be hydrophobic (or to repel the fluid flowing within the interior of the tube). In another embodiment, the radial force element 335 is embedded in the sidewalls (i.e., catheter wall 310) such that it is not in contact with either an exterior surface or an interior surface of the catheter 305. Some embodiments of the disclosure are contemplated as being "floating" embodiments, while others are not.

The radial force element 335 longitudinally distributes force (shown by the point with black arrows) along a length of the tubing. This longitudinal force distribution is greater than that the catheter 305 would have without inclusion of the radial force element 335. Thus, an exterior force impacting a point of the catheter wall 310 is less likely to collapse the tubing (minimizing the interior diameter 315), and more likely to distribute the force (and any compression) along a greater longitudinal cross section of the tubing, which prevents "bottle necking" or pinching of the tubing, where bottle necking otherwise restricts fluid flow. In operation, interspun dynamic (non-static) reinforcements disengage and reengage in a manner without undergoing canula deformation and without substantial polymer or wire separation or deformations when the catheter is flexed, compressed or stretched. The catheter is thus capable of transmitting an axial and co-axial push and pull force against a vascular occlusion in diverse capacities within recommended normal environment to decompress the same and to allow the catheter to improve reliability. As interpreted herein, the catheter may be referred to in its solid nature of cannula and reinforcement as well as fluid flow and delivery.

In one embodiment, inclusion of the radial force element 335 increases the longitudinal elasticity (and compression) of the tubing allowing it to "stretch" and "compress" beyond standard tubes, which ensures the proximal end (in the vessel 306) retains its proper position even when the tube itself is moved.

In one embodiment, the tubing need not be uniform across its entire length, such that the radial force element 335 is restricted to the "critical" sections of the tubing, such as the Insertion Section or the Terminal Section. This minimizes costs for the length of tubing in general, while maximizing the effects by reinforcing the tubing only where most needed. For example, one forth (or less), half, or three fourths of the tubing length may be reinforced in embodiments, where other portions of the tubing are "standard".

In a further embodiment, the length of the tubing need not be uniformly constructed to match the operational concerns present in different lengths. For example, other than the Insertion Section, the exterior diameter of the tubing need not be uniform. In one embodiment, an Expansion Section can exist, which is designed to increase longitudinal expansion/contractions, which improves a motion range of a human patient without movement being experienced at the proximal end 306. For example, a length of tubing on the opposite side of the catheter hub 307 may be intentionally modified to increase movement (expansion/contraction) via use of one or more Expansion Sections. The interior diameter 315 of these Expansion Sections are of concern, as the overall fluid flow must be maintained. However, an exterior diameter need not be constrained (or as constrained as the Insertion Section) as this portion of the tubing is not inserted into a human body. Thus, a portion of the tubing may be protected by an exterior helical coil of metal (not dissimilar to the helical coil of tubing on an exterior of a kink-free garden hose). In one embodiment, the catheter wall 310 diameter of an Expansion Section (supported by a metal helical coil for example) can be thinned, which inherently increases the elasticity of the tubing (depending on the Cannula Material used for the tubing), which decrease does not impede the structural integrity due to the increased support from the metal helical coil. The overall elasticity need not dramatically change to significantly increase the flexibly of the length of tubing itself, which minimizes an effect of movement on the Insertion Section of the tubing. Creatively in adding expansive sections to the tubing is permitted, so long as the overall fluid flow within meets or exceeds the minimal flow thresholds in all situations (i.e., as defined by the Cannula Conventions, for example). Consequently, a paradigm shift for Cannula's is contemplated, such that defining characteristics are not negatively impeded, while striving to improve patient comfort and minimize currently high failure rates (or needs for re-insertions) of conventional IV catheters due to unique design concerns/restrictions inherently in this context unique fluid flow system.

FIG. 3B depicts an example embodiment of the dynamically-reinforced IV catheter having a spiral or spring as the reinforcing member in accordance with embodiments of the inventive arrangements disclosed herein. Specifically, FIG. 3A utilizes a helical coil or reinforcing spiral/spring 335 as a radial force element reinforcing an interior of the catheter tubing. The reinforcing spiral can be stationary (embedded in the sidewalls) or floating having attachment points 340 as previously indicated depending on embodiment.

The spring or helical coil 335 is a resilient device that may be pressed or pulled by is able to return to its former shape when released. The helical coil inherently distributes force applied to a point (perpendicularly) at a horizonal surface, which would otherwise pinch the interior diameter of the tubing and inhibit fluid flow, which addresses sheer stress. In embodiments, the spring 335 can be metal strands to ensure that the overall tubing is effectively the medical equivalent of a wire reinforced hose. In another embodiment, the helical coil can be a non-metal structure, such as a Cannula Materials other than that being primarily used. In other words, the tubing can be formed from a first material and a second different material arranged in a helical coil, such that the material benefits of the combination form a more ideal catheter material than use of either material alone. In different embodiments, the helical coil may be metal materials, non-metal Cannula Material, or other materials such as Directional Glass Fiber Composite Materials and polymers including Glass Fiber Reinforced Polymers (GFRP). Embodiments of the disclosure permit catheters to incorporate advanced materials in possible future without having to compensate on fundamental design and manufacturing principles.

This hybridization of materials and possible variations in manufacturing, through the use of one material being shaped as a helical coil is able to achieve unparallel flexibility and elasticity while still possessing superior anti-kinking properties (resistance to exterior compressive forces that results in comprising the interior diameter and restricting fluid flow) over what is conventionally known/attempted.

FIG. 3C depicts an example embodiment of the dynamically-reinforced IV catheter having a spine with radial ribs as the reinforcing member in accordance with embodiments of the inventive arrangements disclosed herein. Like the helical coil, the rib 350 and spine 345 embodiment can be stationary (embedded in the sidewalls) or floating having attachment points 355 depending on embodiment. One variation includes a reinforcing rib 350 that may consist of a series or set of types circles (or waves) that are positions parallel to the cross section of the tubing. Use of waves provide lower work heights while utilizing the same force, which not only conserves precious space but also smaller assemblies such as the catheter which can utilize fewer materials, leading to lower production cost. Use of waves in embodiments also provide load and radial transmission force rates that more accurate and lower yielding tolerances for certain catheter sizes.

The reinforcing spine 345 is in an attachment relationship with the set of rib 350 elements to ensure the ribs are not displaced. In an embodiment, where the ribs 350 are embedded in a sidewall, the spine 345 may not be needed for positional maintenance. The spine 345 can nevertheless be a force conveying material, used to distribute vibrations/ motion between the rib elements. For example, the reinforcing spine 345 itself can be a longitudinally positioned element adding strength to the length of tubing. More than one spine 345 are possible in embodiments, but care must be taken with regard to material and elasticity of the spine 345 to ensure overall flexibility of the catheter tubing is retained (sufficient for its intended use). The added strength gained through use of the combined spine 345 and rib 350 permit use of otherwise "weak" Cannula Materials to be effectively utilized. As with the inclusion of the spring 335 or helical coil, the spine and rib 350 permit an effective combination of different materials and their properties, which in aggregate (as arranged) result in a more ideal catheter material than possible when utilizing a single material. In different embodiments, the spine 345 and rib 350 may be metal materials, non-metal Cannula Material, or other materials such as polymers.

The diagrams in the Figures illustrate the architecture, functionality, and operation of possible implementations of systems and methods according to various embodiments of the present invention. It will also be noted that each block of the block diagrams and combinations of blocks in the diagrams are not limiting and that one of ordinary skill understands non-shown materials/structures are contemplated for inclusion in derivatives and equivalents of the disclosure presented herein.

What is claimed is:

1. A medical device comprising:

an intravenous (IV) catheter comprising cannula structures consistent with cannula conventions having a cannula formed from cannula materials, said cannula comprising:

a tubing with sidewalls including an inner surface wall, the tubing comprising:

a radial force element configured to reinforce an interior of the tubing, wherein the radial force element is positioned between a first attachment point and a second attachment point, wherein the first attachment point is configured to be positioned outside the skin of the human body when the tubing is inserted into the human body, and the second attachment point is configured to be positioned beyond the skin of the human body when the tubing is inserted into the human body and is located inside a blood vessel of the human body, the radial force element secured to the inner surface wall only at the first and second attachment points and no other affixation points, said radial force element distributing a perpendicular external force, which minimizes decreases in the interior diameter of the tubing to prevent kinks from occurring as a result of simple patient movement.

2. The medical device of claim 1, wherein the radial force element is a helical coil.

3. The medical device of claim 1, the sidewall of the tubing having a uniform exterior diameter and a uniform interior diameter.

4. The medical device of claim 1, wherein the radial force element is metal.

5. The medical device of claim 1, wherein the radial force element is formed from a cannula material different from that that forms an exposed external surface and an interior surface of the tubing.

6. The medical device of claim 1, wherein an exterior diameter of the tubing is configured so that it is not uniform across its entire length and at least a portion of the radial force element is within an insertion section of the tubing.

7. The medical device of claim 1, further comprising an expansion section, wherein the expansion section is longitudinally more compressive and expansive than a terminal section.

8. The medical device of claim 7, wherein the expansion section has an exterior diameter greater than an exterior diameter of the terminal section.

9. The medical device of claim 7, wherein the radial force element is a helical coil, and wherein the helical coil is contained within the expansion section and does not protrude out of an end of the catheter.

10. The medical device of claim 1, wherein the radial force element reinforces a subsection of the tubing where potential kinking problems resulting from patient movement are most prevalent.

11. The medical device of claim 1, wherein the radial force element prevents kinks resulting from motion of environmental items pulling on an exposed portion of the tubing.

12. The medical device of claim 1, wherein the radial force element increases a longitudinal elasticity of the tubing.

13. A medical device comprising:

a cannula formed from cannula materials, said cannula comprising tubing with sidewalls reinforced by a helical coil, the helical coil situated along substantially an entire length of the tubing and secured to the inner sidewall only at first and second attachment points and no other affixation points, which has a uniform exterior diameter and a uniform interior diameter, wherein the helical coil minimizes kinking of the tubing resulting from simple patient movements pulling at the tubing, wherein the helical coil is positioned between a first attachment point and a second attachment point, wherein the first attachment point is configured to be positioned outside the skin of the human body when the tubing is inserted into the human body, and the second attachment point is configured to be positioned beyond the skin of the human body when the tubing is inserted into the human body, and is located inside a blood vessel of the human body.

14. The medical device of claim 13, wherein the helical coil is metal, wherein other than the helical coil, the tubing is made from a uniform, non-metal cannula material.

15. The medical device of claim 13, wherein the helical coil is a first uniform non-metal cannula material, wherein other than the helical coil, the tubing is made from a second uniform non-metal cannula material.

16. The medical device of claim 13, wherein an external diameter of the tubing is not uniform across its entire length and at least a portion of the helical coil is within an insertion section of the tubing.

17. A medical catheter comprising:

a tubing made from a medical grade material, which is a cannula material, of a predetermined gauge and wall thickness consistent with cannula conventions commensurate with an intended medical purpose, the tubing having sidewalls including an inner surface wall;

a hub component coupled to one end of the length of tubing to facilitate attachment to ancillary elements;

a radial force element configured to reinforce an interior of the tubing; and a dynamic reinforcing member positioned along the inner surface wall, wherein the dynamic reinforcing member is configured to resist kinking, wherein the dynamic reinforcing member is positioned between a first attachment point and a second attachment point, wherein the first attachment point is configured to be positioned outside the skin of the human body when the tubing is at least partially inside the human body, and the second attachment point is configured to be positioned beyond the skin of the human body when the tubing is at least partially inside the human body and is located inside a blood vessel of the human body, wherein said reinforcing member provides sufficient outwards radial force to minimize kinking resulting from the external forces, wherein the reinforcing member is coupled to an interior wall of the length of tubing proximate to each end at a specified attachment point, wherein the reinforcing member is able to dynamically adjust its position within the interior space between the first and second attachment points in response to the external forces applied proximate to a skin boundary at an insertion point decreasing a likelihood that the external forces cause the tubing to kink.

18. The medical catheter of claim 17, wherein the radial force element is one of a spring, a helical frame, and a mesh frame.

19. The medical catheter of claim 17, wherein the sidewall of the tubing having a substantially uniform interior and exterior diameter.

20. The medical catheter of claim 17, wherein the dynamic reinforcing member is a discrete section of the medical catheter positioned between the first attachment point and the second attachment point that is not coupled to a discrete actuatable controlling mechanism able to independently control an expansion or contraction of the dynamic reinforcing member, which inherently dynamically adjusts based on its structural integrity in response to application of external forces.

21. The medical catheter of claim 17, wherein the radial force element is embedded in the sidewalls and is not in contact with an exterior surface or an interior surface of the tubing.

* * * * *